(12) United States Patent
McCool et al.

(10) Patent No.: US 10,322,979 B2
(45) Date of Patent: Jun. 18, 2019

(54) ADSORPTIVE SEPARATION OF DIMETHYL BIPHENYL REGIOISOMERS USING 12-MEMBER RING ZEOLITE SORBENTS

(71) Applicant: ExxonMobil Research and Engineering Company, Annandale, NJ (US)

(72) Inventors: Benjamin A. McCool, Annandale, NJ (US); Michael P. Lanci, Flemington, NJ (US); Randall D. Partridge, Califon, NJ (US); Carla S. Pereira, Bridgewater, NJ (US)

(73) Assignee: EXXONMOBIL RESEARCH AND ENGINEERING COMPANY, Annadale, NJ (US)

( * ) Notice: Subject to any disclaimer, the term of this patent is extended or adjusted under 35 U.S.C. 154(b) by 30 days.

(21) Appl. No.: 15/886,115

(22) Filed: Feb. 1, 2018

(65) Prior Publication Data

US 2018/0222824 A1  Aug. 9, 2018

Related U.S. Application Data

(60) Provisional application No. 62/453,190, filed on Feb. 1, 2017.

(51) Int. Cl.

| | |
|---|---|
| C07C 2/74 | (2006.01) |
| B01D 15/08 | (2006.01) |
| C07C 2/66 | (2006.01) |
| C07C 7/13 | (2006.01) |
| C07C 15/14 | (2006.01) |
| B01J 20/28 | (2006.01) |
| B01J 20/18 | (2006.01) |
| C07C 5/10 | (2006.01) |

(Continued)

(52) U.S. Cl.
CPC ............. *C07C 2/74* (2013.01); *B01D 15/08* (2013.01); *B01J 20/186* (2013.01); *B01J 20/28007* (2013.01); *C07C 2/66* (2013.01); *C07C 5/10* (2013.01); *C07C 5/2732* (2013.01); *C07C 5/367* (2013.01); *C07C 7/13* (2013.01); *C07C 15/14* (2013.01)

(58) Field of Classification Search
None
See application file for complete search history.

(56) References Cited

U.S. PATENT DOCUMENTS

| | | |
|---|---|---|
| 3,626,020 A | 12/1971 | Neuzil |
| 3,699,182 A | 10/1972 | Cattanach |

(Continued)

OTHER PUBLICATIONS

Godwin, "Plasticizers", Applied Polymer Science 21st Century, ed. Craver and Carraher, Elsevier (2000), pp. 157-175.

(Continued)

*Primary Examiner* — Tam M Nguyen
(74) *Attorney, Agent, or Firm* — Robert A. Migliorini; Kristina Okafor (57) ABSTRACT

A process for separating dimethyl biphenyl (DMBP) isomers, including contacting a mixture of 3,3'-DMBP, 3,4'-DMBP and 4,4'-DMBP in a first solvent with a 12-member ring zeolite exchanged with potassium or barium, or combinations thereof, and adsorbing the 3,3'-DMBP onto the 12-member ring zeolite, such as by passing the mixture through at least one packed bed of the potassium and/or barium exchanged 12-member ring zeolite.

16 Claims, 4 Drawing Sheets

(51) Int. Cl.
*C07C 5/27* (2006.01)
*C07C 5/367* (2006.01)

(56) References Cited

U.S. PATENT DOCUMENTS

| | | | |
|---|---|---|---|
| 6,274,756 B1 | 8/2001 | Caers et al. | |
| 6,730,625 B1 | 5/2004 | Chang et al. | |
| 8,580,120 B2 | 11/2013 | Porter | |
| 8,829,093 B2 | 9/2014 | Dakka et al. | |
| 9,085,669 B2 | 7/2015 | Dakka et al. | |
| 9,328,053 B2 | 5/2016 | Bai et al. | |
| 9,556,103 B2 * | 1/2017 | Dakka | C07C 67/035 |
| 9,580,572 B2 | 2/2017 | Dakka et al. | |
| 9,663,417 B2 | 5/2017 | Dakka et al. | |
| 9,688,602 B2 * | 6/2017 | Dakka | C07C 67/08 |
| 2009/0299111 A1 * | 12/2009 | Kanbara | C07C 2/862 |
| | | | 585/23 |
| 2015/0080546 A1 * | 3/2015 | Dakka | C07C 51/265 |
| | | | 528/305 |
| 2015/0361011 A1 * | 12/2015 | Salciccioli | C07C 5/367 |
| | | | 585/252 |
| 2016/0176785 A1 * | 6/2016 | Salciccioli | C07C 5/367 |
| | | | 585/320 |

OTHER PUBLICATIONS

Minceva et al., "Modeling and simulation of a moving bed for the separation of p-xylene", Ind. Eng. Chem. Res., 2002, vol. 41, pp. 3454-3461.

Minceva et al., "Understanding and revamping of industrial scale SMB units for p-sylene separation", AIChE J., 2007, vol. 53, pp. 138-149.

Rajendran et al., "Simulated moving bed chromatography for the separation of enantiomers", J. Chromatography A, 2009, vol. 1216, pp. 709-738.

Ruthven et al., "Counter-current and simulated counter-current adsorption separation processes", Chem. Eng. Sci., 1989, vol. 44, pp. 1011-1038.

Silva et al., "Fixed-bed adsorption of aromatic C8 isomers: breakthrough experiments, modeling and simulation", Sep. Pur. Tech., 2012, vol. 90, pp. 246-256.

Silva et al., "Modeling and simulation of an industrial-scale parex process", AIChE J., 2015, vol. 61, pp. 1345-1363.

* cited by examiner

ADSORPTIVE SEPARATION OF DIMETHYL BIPHENYL REGIOISOMERS USING 12-MEMBER RING ZEOLITE SORBENTS

CROSS-REFERENCE TO RELATED APPLICATIONS

This application claims the benefit of U.S. Provisional Application No. 62/453,190, filed on Feb. 1, 2017, the entire contents of which are incorporated herein by reference.

FIELD

Disclosed are processes for separation of dimethylbiphenyl regioiosmers.

BACKGROUND

Plasticizers are incorporated into a resin (usually a plastic or elastomer) to increase the flexibility, workability, or dispensability of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002.

It would be advantageous to develop a new generation of plasticizers with improved performance compared to phthalate esters.

SUMMARY

Presented herein is a process for separating dimethyl biphenyl (DMBP) isomers, comprising contacting a mixture of 3,3'-DMBP, 3,4'-DMBP and 4,4'-DMBP with a 12-member ring zeolite exchanged with potassium or barium, or combinations thereof.

In one form, the 12-member ring zeolite is exchanged with potassium.

In another form, the 12-member ring zeolite is exchanged with barium.

In another form, the 12-member ring zeolite is one of zeolite X (K—X) or zeolite V (K—Y).

In yet another form, the 12-member ring zeolite is one of barium and potassium-exchanged zeolite X (BaK—X) or barium and potassium-exchanged zeolite Y (BaK—Y).

Advantageously, the isomer mixture is contained in a solvent which does not adsorb onto the 12-member ring zeolite.

According to the process, the 3,3'-DMBP isomer is more strongly adsorbed onto the 12-member ring zeolite than the 3,4'-DMBP and 4,4'-DMBP isomers.

Additionally presented is a process for separating dimethyl biphenyl (DMBP) isomers, comprising passing a mixture of 3,3'-DMBP, 3,4'-DMBP and 4,4'-DMBP in a first solvent through at least one packed bed of 12-member ring zeolite exchanged with potassium or barium, or combinations thereof, and adsorbing the 3,3'-DMBP onto the 12-member ring zeolite.

In one form, the 12-member ring zeolite is exchanged with potassium.

In another form, the 12-member ring zeolite is exchanged with barium.

In another form, the 12-member ring zeolite is one of zeolite X (K—X) or zeolite Y (K—Y).

In yet another form, the 12-member ring zeolite is one of barium and potassium-exchanged zeolite X (BaK—X) or barium and potassium-exchanged zeolite Y (BaK—Y).

Advantageously, the first solvent does not adsorb onto the 12-member ring zeolite.

In one form, the 3,3'-DMBP is more strongly adsorbed onto the 12-member ring zeolite than the 3,4'-DMBP and 4,4'-DMBP isomers.

In another form, the packed bed of 12-member ring zeolite is in a chromatographic column and the packed bed has an inlet and an outlet.

In yet another form, the process further comprises collecting a raffinate mixture of 3,4'-DMBP and 4,4'-DMBP isomers at the outlet of the packed bed substantially before the 3,3'-DMBP isomer reaches the outlet of the packed bed.

In one form, the process further comprises passing the raffinate mixture through multiple chromatographic columns containing packed beds of 12-member ring zeolite in a simulated moving bed separation system.

In another form, the process further comprises desorbing the 3,3'-DMBP from the 12-member ring zeolite with a second solvent.

BRIEF DESCRIPTION OF THE DRAWINGS

The present disclosure is susceptible to various modifications and alternative forms, specific exemplary implementations thereof have been shown in the drawings and are herein described in detail. It should be understood, however, that the description herein of specific exemplary implementations is not intended to limit the disclosure to the particular forms disclosed herein.

DETAILED DESCRIPTION

There is an increased interest in developing new plasticizers which possess good plasticizer performance characteristics but are still competitive economically. The present disclosure is directed towards separation of methyl biphenyl OXO-ester precursors.

Definitions

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of the present invention described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

The term dimethylbiphenyl (DMBP) refers to the compounds to be separated by the presently described processes, having the following general chemical structure:

The isomers of interest for making plasticizers are primarily 3,4'-dimethyl-1,1'-biphenyl and 4,4'-dimethyl-1,1'-biphenyl. For convenience, the structure below is shown as the 4,4'- isomer, but it will be understood that the 3,3'- and 3,4'-isomers are also covered by the general terminology.

The term "M-Acid" refers to a mono-carboxylic acid of a DMBP molecule, in particular 4'-methyl-1,1'-biphenyl-4-carboxylic acid, a desired product of the present processes. The chemical structure of methyl-1,1'-biphenyl-carboxylic acid is:

An "OXO-ester" is a compound having at least one functional ester moiety within its structure derived from esterification of either an acid or alcohol compound with an OXO-alcohol or OXO-acid, respectively.

An "OXO-alcohol" is an organic alcohol, or mixture of organic alcohols, which is prepared by hydroformylating an olefin, followed by hydrogenation to form the alcohols. Typically, the olefin is formed by light olefin oligomerization over heterogenous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. The OXO-alcohols consist of multiple isomers of a given chain length due to the various isomeric olefins obtained in the oligomerization process, in tandem with the multiple isomeric possibilities of the hydroformylation step.

One potential route to new plasticizers is producing biphenyl-based plasticizers from toluene hydroalkylation followed by dehydrogenation to produce a mixture of dimethylbiphenyl (DMBP) isomers.

Figure 1:
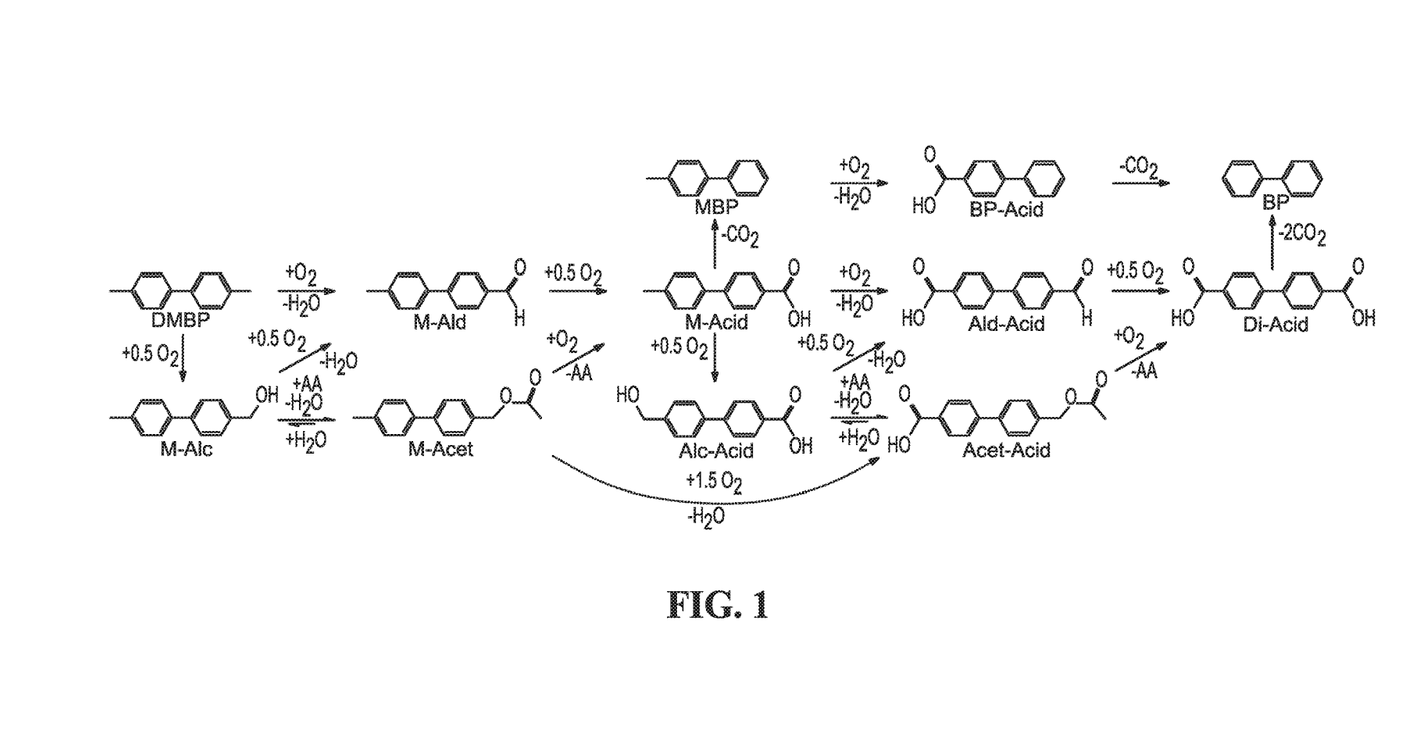
FIG. 1 shows a number of possible reaction pathways for oxidation of 4,4'-DMBP.

The DMBP molecules can be oxidized to produce many molecules. FIG. 1 shows some of the pathways that exist, the dashed arrows representing multiple reaction steps. The desired oxidation products are methyl-1,1'-biphenyl-carboxylic acids (mono-acids or M-acid). The acid groups can be esterified with OXO-alcohols to produce esters and when the methyl and carboxylic acid groups are on adjacent rings in the 3- or 4-positions, the final esters have excellent plasticizer properties.

The mono-aldehyde (M-Ald), mono-alcohol (M-Alc) and mono-acetate (M-Acet) molecules are considered to be under-oxidized, but are relatively easily converted to the M-Acid. These under-oxidized molecules can be recycled into the oxidation reaction for conversion to M-Acids. In contrast, the aldehyde-acid (Ald-Acid), acetate-acid (Acet-Acid) and Di-Acid molecules are considered to be over-oxidized, and coversion back to an M-Acid is more difficult.

Figure 2:
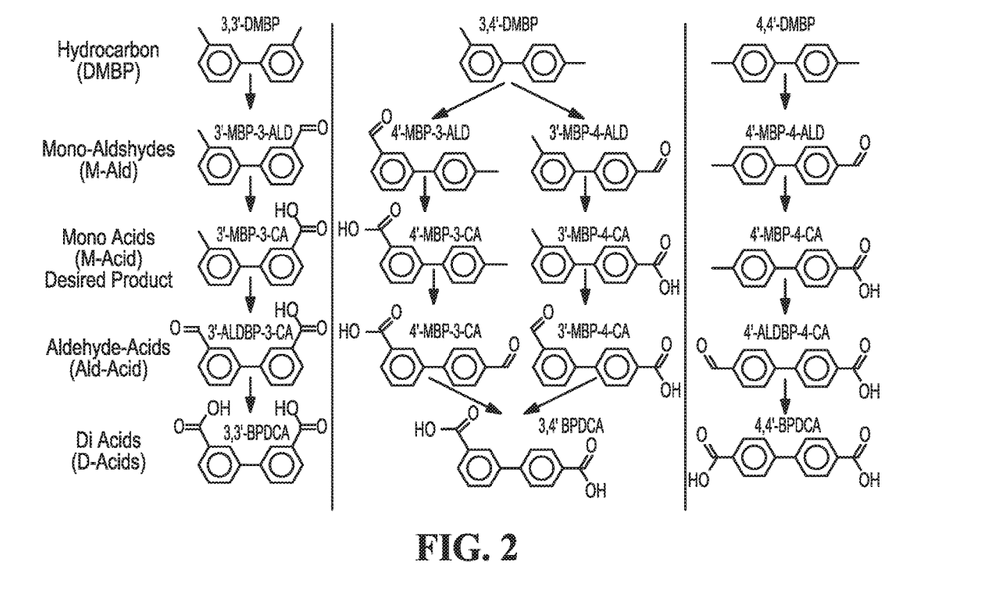
FIG. 2 shows potential oxidation products resulting from oxidation of biphenyl isomers mixtures.

DMBP is produced as a mixture of isomers and while the 2,3'- and 2,4'-isomers can be separated from the 3,3'-, 3,4'-, and 4,4'-DMBP isomers by distillation, additional separation of the latter is very expensive. Therefore, oxidation of a mixture of 3,3'-, 3,4'- and 4,4'-isomers is desirable, but it has been discovered that the selective oxidation of this mixture is also much more complex than any of the individual isomers. FIG. 2 illustrates some of the more abundant intermediates and isomers of intermediates of the reaction. The over-oxidized products, Ald-Acids and Di-Acids, represent yield loss because no market or feasible method of recovering them as M-Acids currently exists. Stopping the oxidation reaction at the M-Acids with high selectively for each isomer in a mixture is hampered by the fact that each isomer oxidizes at very different reaction rates. For example, pure 4,4'-DMBP oxidizes approximately 80 times faster than pure 3,3'-DMBP. As shown in Table 1, at 50% conversion of a mixture of the three isomers, the 4,4'-isomer will typically reach 99% conversion before 3,3'-isomer reaches 20% conversion, and this leads to significant yields of unusable over-oxidized products.

TABLE 1

Yields of isomers at 50% conversion total DMBP

| Isomer | M-Ald | M-Acid | Ald-Acid | Di-Acid | % Isomer Conversion |
|---|---|---|---|---|---|
| 3,3'-DMBP | 6.6% | 14.3% | 0.4% | 0.6% | 20.4% |
| 3,4'-DMBP | 17.1% | 57.9% | 1.8% | 1.1% | 83.8% |
| 4,4'-DMBP | 7.2% | 71.5% | 4.1% | 1.6% | 99.7% |

Figure 3:
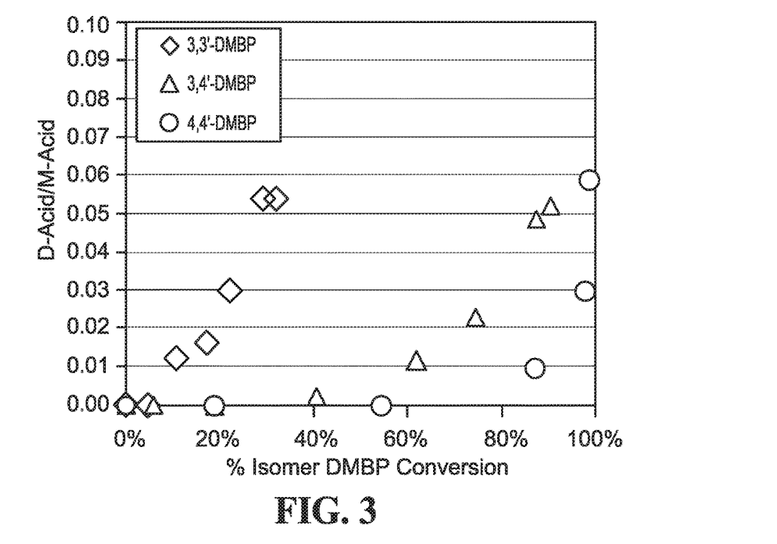
FIG. 3 shows the di-acid to mono-acid ratio as a function of conversion for the three DMBP isomers.

FIG. 3 illustrates the effect that the large difference in rates of reactivity between the isomers has on the ratios of Di-Acid and M-Acid for each isomer. The purification of M-Acid is also challenged by having a mixture of isomers. Taking melting point as an indicator of relative solubility (M.P. correlates inversely with solubility), the 3,3'-M-acid (M.P. 133.7° C.) has as very similar melting point as 4.4'-DMBP (M.P. 121.4° C.) and 4,4'-M-aldehyde (M.P. 105.9° C.). It has been determined that this causes the 3,3'-M-acid isomer to be difficult to precipitate from the product mixture, resulting in 3,3'-M-acid to be recycled with the unreacted DMBP to the oxidation reactor where it becomes over-oxidized. The presence of soluble 3,3'-M-acid also enhances the solubility of the 3,4'- and 4,4'-M-acid isomers, pulling them into the recycle stream as well. The net result is a nearly entire yield loss of the 3,3'-isomer and low yields of the 3,4'- and 4,4'-M-acids.

According to the presently disclosed process, 3,3'-DMBP can be effectively separated from 3,4'- and 4,4'-DMBP, thus permitting the selective oxidation of the latter two compounds to proceed more efficiently.

Separation of the 3,3'-, 3,4'- and 4,4'-DMBP isomers can be accomplished by adsorptive separations in the liquid phase. In particular, certain potassium and/or barium exchanged 12-member ring zeolites, particularly potassium-exchanged zeolite X (K—X) and zeolite Y (K—Y) have been demonstrated to adsorb 3,3'-DMBP much more strongly than the 3,4'- and 4,4'-isomers. Additionally, barium and potassium-exchanged zeolite X (BaK—X) and zeolite Y (BaK—Y) have been demonstrated to be effective for the same separation.

The process for separating dimethyl biphenyl (DMBP) isomers includes passing a mixture of 3,3'-DMBP, 3,4'-DMBP and 4,4'-DMBP in a first solvent through at least one packed bed of potassium and/or barium exchanged 12-member ring zeolites and adsorbing the 3,3'-DMBP onto the 12-member ring zeolites.

The solvent should be selected such that it does not adsorb onto the 12-member ring zeolites. Suitable solvents include iso-octane and cyclohexane.

The separation factor for the 3,3'-DMBP was determined to be 1.7, which suggests that the separation can be performed continuously on a simulated moving bed (SMB) apparatus, wherein multiple packed beds, such as chromatographic columns, of the potassium and/or barium exchanged 12-member ring zeolites are arranged in series and in a closed circuit, having a feed stream inlet and a desorbent inlet, at least one raffinate outlet and at least one extract outlet. The 3,4'-DMBP and 4,4'-DMBP can be removed as a raffinate, and the 3,3'-DMBP extract subsequently desorbed, advantageously with a different solvent, such as toluene, xylene, ethyl benzene or tetrahydrofuran.

EXAMPLES

Column Preparation

Several adsorbents (K—Y, BaK—Y and K—X) were evaluated for separations of DMBP isomers. The adsorbents were densely packed into 4.6 mm ID×100 mm length stainless steel columns, and 0.5 micrometer frits were placed at each end. The adsorbents were dried at 300° C. for 1 hour in a flow of dry nitrogen. Iso-octane (2,2,4-trimethylpentane, HPLC grade from Sigma-Aldrich) was used as the eluent solvent at a flowrate of about 0.35 ml/min, while maintaining a backpressure on the column of about 10 bar or greater. The evaluation temperature was about 177° C.

Example 1

Figure 4:
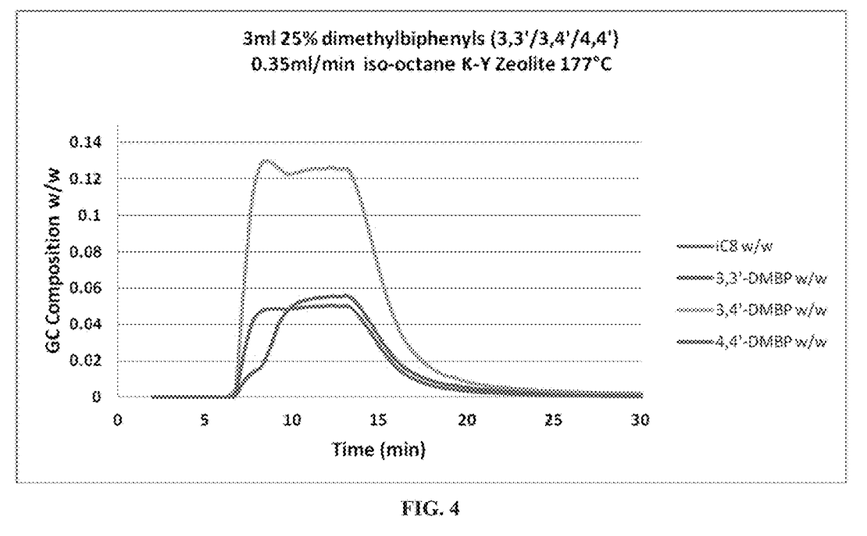
FIG. 4 shows the breakthrough curves for a mixture of 3,3'-DMBP, 3,4'-DMBP and 4,4'-DMBP fed into a K—Y packed column.

A 3 ml pulse of 25 wt % DMBP isomer mixture in iso-octane was introduced to the K—Y column. FIG. 4 shows the breakthrough curves for a mixture of 3,3'-DMBP, 3,4'-DMBP and 4,4'-DMBP fed into the K—Y packed column. The 3,3'-isomer was clearly retained as compared to the 4,4'-isomer and the 3,4'-isomer. The selectivity was calculated to be 1.7 as compared to the 3,4'-isomer, and 1.75 as compared to the 4,4'-isomer.

Example 2

Figure 5:
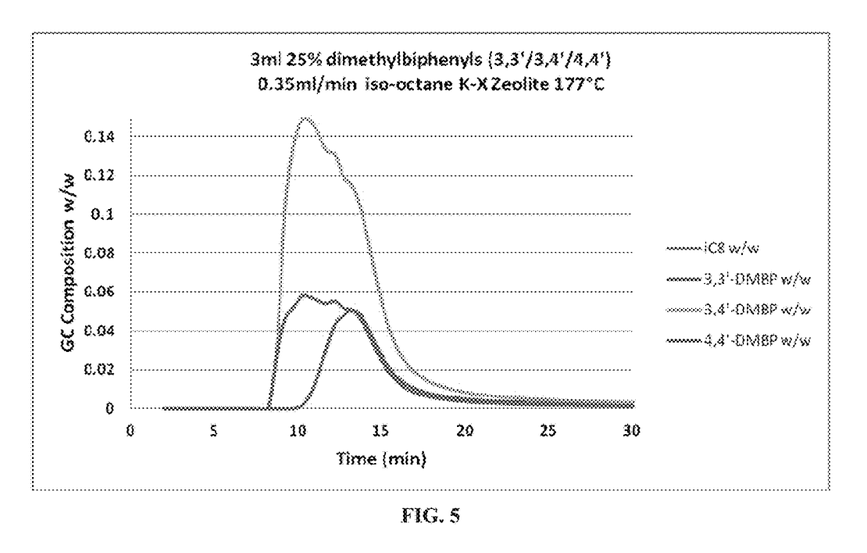
FIG. 5 shows the breakthrough curves for a mixture of 3,3'-DMBP, 3,4'-DMBP and 4,4'-DMBP fed into a K—X packed column.

A 3 ml pulse of 25 wt % DMBP isomer mixture in iso-octane was introduced to the K—X column. FIG. 5 shows the breakthrough curves for a mixture of 3,3'-DMBP, 3,4'-DMBP and 4,4'-DMBP fed into the K—X packed column. The 3,3'-isomer was clearly retained as compared to the 4,4'-isomer and the 3,4'-isomer.

Example 3

Figure 6:
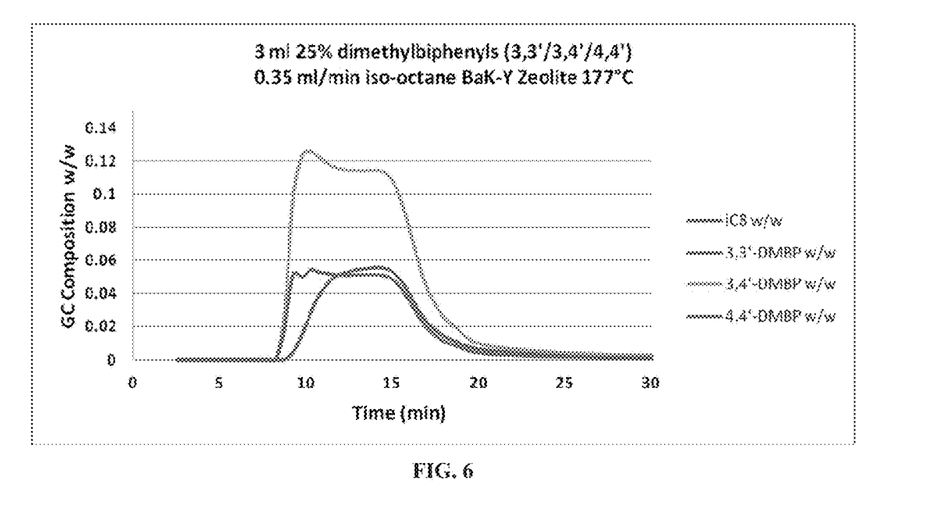
FIG. 6 shows the breakthrough curves for a mixture of 3,3'-DMBP, 3,4'-DMBP and 4,4'-DMBP fed into a BaK—Y packed column.

A 3 ml pulse of 25 wt % DMBP isomer mixture in iso-octane was introduced to the BaK—Y column. FIG. 6 shows the breakthrough curves for a mixture of 3,3'-DMBP, 3,4'-DMBP and 4,4'-DMBP fed into the BaK—Y packed column. The 3,3'-isomer was clearly retained as compared to the 4,4'-isomer and the 3,4'-isomer.

Example 4

Figure 7:
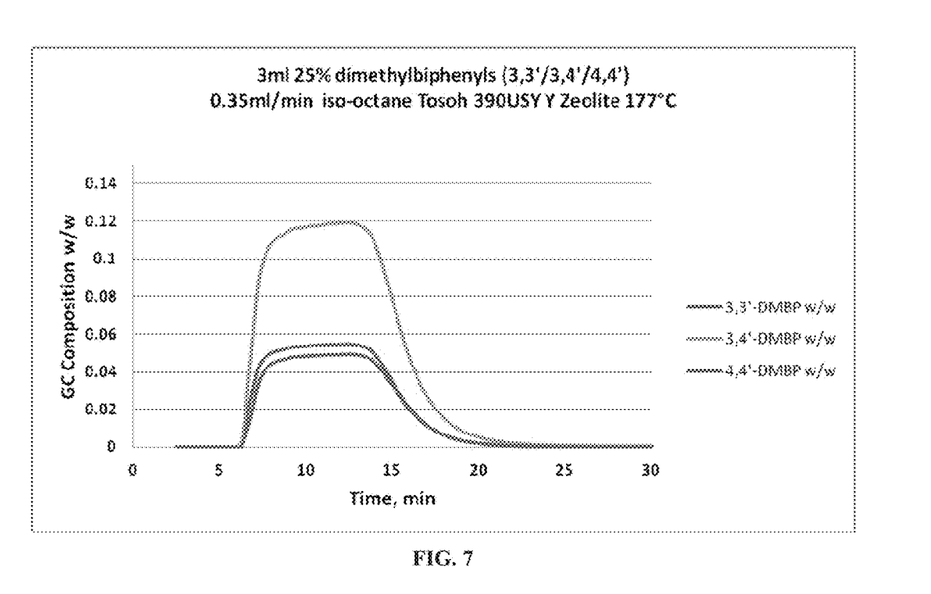
FIG. 7 shows the breakthrough curves for a mixture of 3,3'-DMBP, 3,4'-DMBP and 4,4'-DMBP fed into a high silica USY packed column.

For comparison and to illustrate the effect of cations present in the zeolite, a high silica faujasite (390 USY) was packed into a column, prepared and tested under the same conditions as set forth in the examples above. FIG. 7 shows that the high silica faujasite without cations demonstrates no selectivity for any of the isomers over the others.

Further illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT Clauses:

1. A process for separating dimethyl biphenyl (DMBP) isomers, comprising contacting a mixture of 3,3'-DMBP, 3,4'-DMBP and 4,4'-DMBP with a 12-member ring zeolite exchanged with potassium or barium, or combinations thereof.

2. The process of paragraph 1, wherein the 12-member ring zeolite is exchanged with potassium.

3. The process of paragraph 1, wherein the 12-member ring zeolite is exchanged with barium.

4. The process of paragraph 2, wherein the 12-member ring zeolite is one of zeolite X (K—X) or zeolite Y (K—Y).

5. The process of paragraph 1, wherein the 12-member ring zeolite is one of barium and potassium-exchanged zeolite X (BaK—X) or barium and potassium-exchanged zeolite Y (BaK—Y).

6. The process of any of paragraphs 1 to 5, wherein the isomer mixture is contained in a solvent which does not adsorb onto the 12-member ring zeolite.

7. The process of any of paragraphs 1 to 6, wherein the 3,3'-DMBP isomer is more strongly adsorbed onto the 12-member ring zeolite than the 3,4'-DMBP and 4,4'-DMBP isomers.

8. A process for separating dimethyl biphenyl (DMBP) isomers, comprising passing a mixture of 3,3'-DMBP, 3,4'-DMBP and 4,4'-DMBP in a first solvent through at least one packed bed of 12-member ring zeolite exchanged with potassium or barium, or combinations thereof, and adsorbing the 3,3'-DMBP onto the 12-member ring zeolite.

9. The process of paragraph 8, wherein the 12-member ring zeolite is exchanged with potassium.

10. The process of paragraph 8, wherein the 12-member ring zeolite is exchanged with barium.

11. The process of paragraph 8, wherein the 12-member ring zeolite is one of zeolite X (K—X) or zeolite Y (K—Y).

12. The process of paragraph 8, wherein the 12-member ring zeolite is one of barium and potassium-exchanged zeolite X (BaK—X) or barium and potassium-exchanged zeolite Y (BaK—Y).

13. The process of any of paragraphs 8 to 12, wherein the first solvent does not adsorb onto the 12-member ring zeolite.

14. The process of any of paragraphs 8 to 13, wherein the 3,3'-DMBP is more strongly adsorbed onto the 12-member ring zeolite than the 3,4'-DMBP and 4,4'-DMBP isomers.

15. The process of any of paragraphs 8 to 14, wherein the packed bed of 12-member ring zeolite is in a chromatographic column and the packed bed has an inlet and an outlet.

16. The process of paragraph 15, further comprising collecting a raffinate mixture of 3,4'-DMBP and 4,4'-DMBP isomers at the outlet of the packed bed substantially before the 3,3'-DMBP isomer reaches the outlet of the packed bed.

17. The process of paragraph 14, further comprising passing the raffinate mixture through multiple chromatographic columns containing packed beds of 12-member ring zeolite in a simulated moving bed separation system.

18. The process of any of paragraphs 8 to 17, further comprising desorbing the 3,3'-DMBP from the 12-member ring zeolite with a second solvent.

INDUSTRIAL APPLICABILITY

The systems and methods disclosed herein are applicable to the chemical industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A process for separating 3,3'-dimethyl biphenyl (DMBP) isomers from a mixture of 3,3'-DMBP, 3,4'-DMBP and 4,4'-DMBP isomers, the process comprising contacting the mixture with a 12-member ring zeolite exchanged with potassium or barium, or combinations thereof, wherein the 3,3'-DMBP isomer is more strongly adsorbed onto the 12-member ring than the 3-4'-DMBP and 4,4'-DMBP isomers.

2. The process of claim 1, wherein the 12-member ring zeolite is exchanged with potassium.

3. The process of claim 1, wherein the 12-member ring zeolite is exchanged with barium.

4. The process of claim 2, wherein the 12-member ring zeolite is one of zeolite X (K—X) or zeolite Y (K—Y).

5. The process of claim 1, wherein the 12-member ring zeolite is one of barium and potassium-exchanged zeolite X (BaK—X) or barium and potassium-exchanged zeolite Y (BaK—Y).

6. The process of claim 1, wherein the isomer mixture is contained in a solvent which does not adsorb onto the 12-member ring zeolite.

7. A process for separating 3,3'-dimethyl biphenyl (DMBP) isomers from a mixture of 3,3'-DMBP, 3,4'-DMBP and 4,4'-DMBP isomers, the process comprising passing the mixture in a first solvent through at least one packed bed of 12-member ring zeolite exchanged with potassium or barium, or combinations thereof, wherein the 3,3'-DMBP is more strongly adsorbed onto the 12-member ring zeolite than the 3,4'-DMBP and 4,4'-DMBP isomers.

8. The process of claim 7, wherein the 12-member ring zeolite is exchanged with potassium.

9. The process of claim 7, wherein the 12-member ring zeolite is exchanged with barium.

10. The process of claim 7, wherein the 12-member ring zeolite is one of zeolite X (K—X) or zeolite Y (K—Y).

11. The process of claim 7, wherein the 12-member ring zeolite is one of barium and potassium-exchanged zeolite X (BaK—X) or barium and potassium-exchanged zeolite Y (BaK—Y).

12. The process of claim 7, wherein the first solvent does not adsorb onto the 12-member ring zeolite.

13. The process of claim 7, wherein the packed bed of 12-member ring zeolite is in a chromatographic column and the packed bed has an inlet and an outlet.

14. The process of claim 13, further comprising collecting a raffinate mixture of 3,4'-DMBP and 4,4'-DMBP isomers at the outlet of the packed bed substantially before the 3,3'-DMBP isomer reaches the outlet of the packed bed.

15. The process of claim 14, further comprising passing the raffinate mixture through multiple chromatographic columns containing packed beds of 12-member ring zeolite in a simulated moving bed separation system.

16. The process of claim 7, further comprising desorbing the 3,3'-DMBP from the 12-member ring zeolite with a second solvent.

* * * * *